United States Patent
Jansheski

(10) Patent No.: US 9,622,837 B2
(45) Date of Patent: Apr. 18, 2017

(54) DENTAL GUARD WITH TEMPORARY FORMING TRAY

(75) Inventor: John M. Jansheski, Maryville, TN (US)

(73) Assignee: DenTek Oral Care, Inc., Tarrytown, NY (US)

( * ) Notice: Subject to any disclaimer, the term of this patent is extended or adjusted under 35 U.S.C. 154(b) by 998 days.

(21) Appl. No.: 13/081,853

(22) Filed: Apr. 7, 2011

(65) Prior Publication Data
US 2011/0247635 A1    Oct. 13, 2011

Related U.S. Application Data

(60) Provisional application No. 61/322,140, filed on Apr. 8, 2010.

(51) Int. Cl.
*A61C 5/14*    (2006.01)
*A61C 9/00*    (2006.01)

(52) U.S. Cl.
CPC .................. *A61C 9/0006* (2013.01)

(58) Field of Classification Search
CPC .................................... A61C 9/0006
USPC .................. 128/862, 861; 433/6, 37
See application file for complete search history.

(56) References Cited

U.S. PATENT DOCUMENTS

| | | |
|---|---|---|
| 1,663,695 A | 3/1928 | Foster |
| 2,705,492 A | 4/1955 | Chandler |
| 2,706,478 A | 4/1955 | Porter |
| 2,750,941 A | 6/1956 | Cathcart |
| 2,827,899 A | 3/1958 | Altieri |
| 3,016,052 A | 1/1962 | Zubren |
| 3,107,668 A | 10/1963 | Thompson |
| 3,124,129 A | 3/1964 | Grossberg |
| 3,224,441 A | 12/1965 | Monaghan |
| 3,250,272 A | 5/1966 | Greenberg |
| 3,379,193 A | 4/1968 | Monaghan |
| 3,411,501 A | 11/1968 | Greenberg |
| 4,063,552 A | 12/1977 | Going |
| 4,668,188 A | 5/1987 | Wolfenson |
| 4,776,792 A * | 10/1988 | Wagner et al. .................. 433/71 |
| 5,415,544 A | 5/1995 | Oxman |
| 5,562,449 A * | 10/1996 | Jacobs et al. .................. 433/215 |
| 5,566,684 A | 10/1996 | Wagner |
| 5,616,027 A | 4/1997 | Jacobs |
| 5,769,633 A | 6/1998 | Jacobs |
| 5,807,100 A | 9/1998 | Thornton |
| 6,581,604 B2 | 6/2003 | Cook |
| 6,820,623 B2 | 11/2004 | Cook |
| 6,830,051 B1 | 12/2004 | Lesniak |
| D504,744 S | 5/2005 | Hidalgo |
| 7,305,990 B2 | 12/2007 | Mathias |
| 7,658,193 B2 | 2/2010 | Lesniak |
| 7,954,496 B2 * | 6/2011 | Jansheski et al. ............. 128/859 |
| 2003/0054316 A1 * | 3/2003 | Cozzi .............................. 433/37 |

* cited by examiner

*Primary Examiner* — Victoria J Hicks
(74) *Attorney, Agent, or Firm* — Luedeka Neely Group, PC

(57) ABSTRACT

A dental guard system for fitting boil and bite dental guards so that undesirable deformations of the guard are avoided during the fitting of the guard to the user. The system includes a boil and bite dental guard and an associated forming tray configured to be generally rigid but conformable in that it tends to retain its shape so as to inhibit undesirable deformations of the guard, yet enables the guard to form to the teeth of the user.

3 Claims, 4 Drawing Sheets

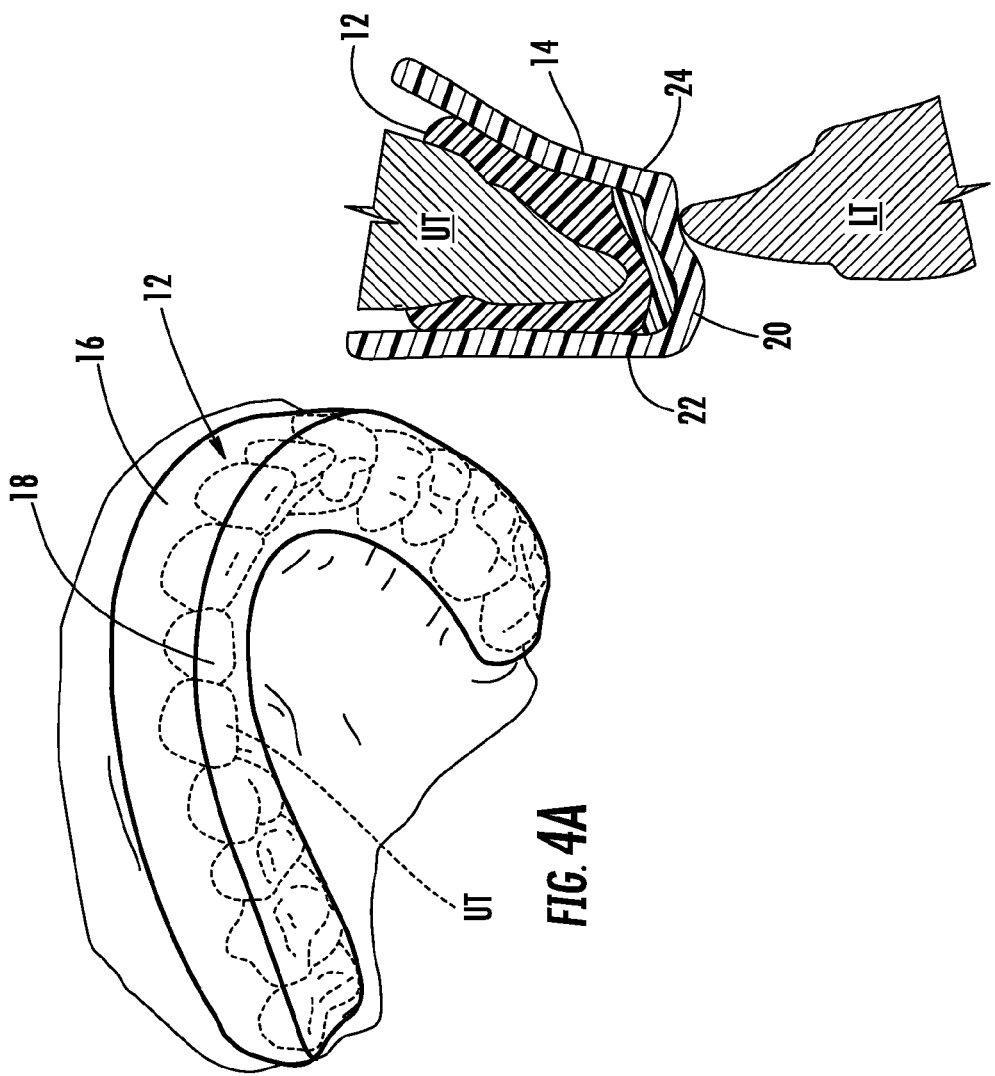

DENTAL GUARD WITH TEMPORARY FORMING TRAY

CROSS-REFERENCE To RELATED APPLICATION

This application claims priority to U.S. Provisional Application Ser. No. 61/322,140 filed Apr. 8, 2010, and entitled DENTAL GUARD WITH TEMPORARY FORMING TRAY, incorporated by reference herein in its entirety.

FIELD

The present disclosure relates to dental guard devices. More particularly, the disclosure relates to a system for improving fit of boil and bite type dental guards.

BACKGROUND

Improvement is desired in the fitting of so-called "boil and bite" dental guards to the teeth of a user. These dental guards are made out of thermoformable materials, such as thermoplastics. Typically, a user heats water to boiling and immerses the guard in the water until the plastic becomes pliable (e.g. 30 seconds). The user then places the guard in this pliable state in his mouth and applies biting pressure to conform the guard to the teeth. The guard is then cooled to retain the bite pattern in the material.

Boil and bite guards are popular because they offer some customization of the guard to the user and are relatively inexpensive. Boil and bite dental guards are commonly configured for various dental guard needs, including sports mouthguards and as nightguards for use in inhibiting nighttime grinding of teeth (Bruxism) while a user sleeps.

Boil and bite dental guards have various shortcomings. Traditional boil and bite dental guards, being made of a moldable material, are fitted by placing the guard in heated or boiling water to make the guard malleable, removing the guard from the water and aligning the guard with the upper teeth. The user then bites down on the guard to form an impression in the moldable material. The user then continues to fit the dental guard by pushing the guard material with the finger tips and tongue to form an impression against the buccal and lingual walls. The use of the fingers and tongue to form the guard causes an uneven distribution of pressure against the buccal and lingual walls and thus an uneven distribution of material. As the material cools, it begins to set. As the material cools it becomes less pliable and resistant to forming an impression with the buccal and lingual walls. As a result, often during this customization step, portions of the material can undesirably spread, distort, or otherwise deform in response to the application of bite pressure and pressure applied the user's fingers and tongue. Various portions of the formed guard can become too thin or too thick, and portions can become positioned so as to be uncomfortable to the user.

What is needed is improvement in the fitting of boil and bite dental guards so that undesirable deformations of the guard are avoided during the fitting of the guard to the user.

SUMMARY

The above and other needs are met by a dental guard system having a boil and bite dental guard and an associated forming tray configured to be generally rigid but conformable in that it tends to retain its shape so as to inhibit undesirable deformations of the guard, yet enables the guard to form to the teeth, the surrounding tissue and the supporting structure of the user.

The tray of this dental guard system reduces or eliminates the need to form the moldable dental guard material against the buccal and lingual walls with the fingers or tongue. The tray engages the lower tooth surfaces permitting the user to apply a biting pressure during fitting of the guard to provide a custom fit guard such that the material of a tooth receiving channel of the guard is directed over the teeth, the surrounding tissue and the supporting structure of the user resulting in an impression that more closely conforms to the dental topographies of the user and allowing for a closer and more even custom fit.

In a preferred embodiment, a dental guard system according to the disclosure includes a boil and bite dental guard having an impressionable channel and a pair of guard sidewalls on opposite sides of the channel. The guard changes configuration when being fitted to a user by use of heating of the guard followed by application of biting pressure by the user.

The system also includes a forming tray configured to fittingly receive the dental guard during heating and fitting of the dental guard to teeth of the user and to support the dental guard and inhibit undesirable deformations of the guard during fitting of the guard to the user characterized by areas of the guard becoming undesirably bulged or undesirably thin or both.

The tray is configured to expand slightly to receive the guard, and thereafter relax to grip and retain the guard during heating and fitting of the guard, with the guard being removed from the tray after the guard is fitted to the user. The tray has a base and upstanding tray sidewalls on opposite sides of the base defining borders of the tray. The tray sidewalls extend higher than the guard sidewalls so as to fully contain the guard as it changes configuration during fitting such that portions of the guard do not pass beyond the borders of the tray and the tray constrains the guard to inhibit the undesirable deformations of the guard during fitting of the guard to the user.

BRIEF DESCRIPTION OF THE DRAWINGS

Further advantages of the disclosure are apparent by reference to the detailed description when considered in conjunction with the figures, which are not to scale, so as to more clearly show the details, wherein like reference numbers indicate like elements throughout the several views, and wherein:

FIG. 4A is a perspective view showing a boil and bite type dental guard applied to the teeth of a user utilizing a forming tray according to the disclosure. FIG. 4B is a cross-sectional view showing use of the forming tray. FIG. 4C is a cross-sectional view showing the dental guard after installation and removal of the forming tray, with the installed dental guard being substantially free of undesired deformations.

DETAILED DESCRIPTION

Figure 1:
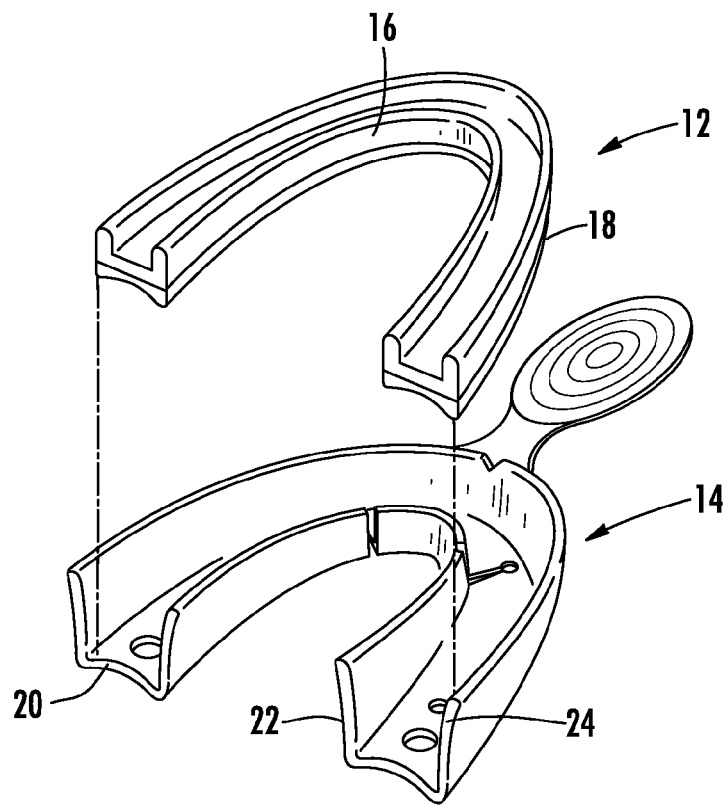
FIG. 1 is an exploded perspective view of a dental guard system having a boil and bite type dental guard and a forming tray according to the disclosure.
Figure 2:
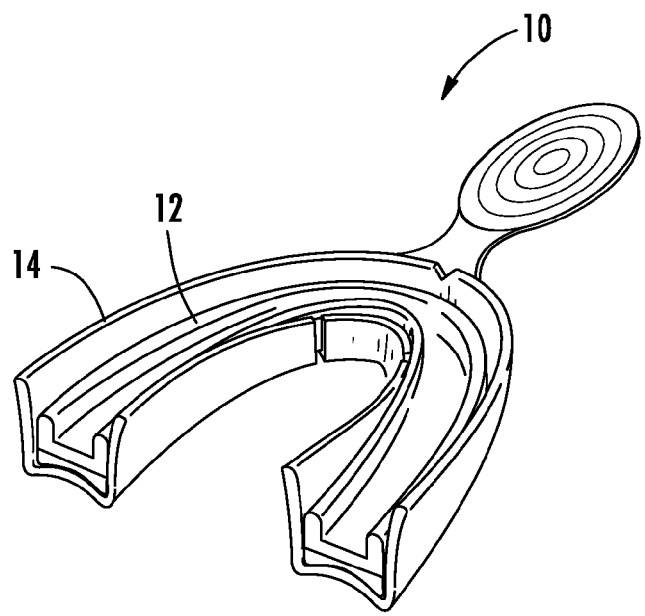
FIG. 2 is an assembled view of the dental guard system of FIG. 1.

With reference to the drawings, the disclosure relates to a dental guard system 10 for fitting of boil and bite dental guards so that undesirable deformations of the guard are avoided during the fitting of the guard to the user. The system 10 includes a boil and bite dental guard 12 and an associated forming tray 14.

The guard 12 may be configured for various uses, such as a mouthguard for sports or a nightguard for inhibiting bruxism. A particularly preferred guard 12 is a u-shaped night guard configured for inhibiting bruxism and available under the trade mark CUSTOM COMFORT from Dentek Oral Care, Inc. of Maryville, Tenn. The CUSTOM COMFORT nightguard includes a u-shaped bite channel 16 made of a thermoplastic material that softens when immersed in boiling water and provides a "boil and bite" fitting function.

A tooth pad 18 is located opposite the channel 16 for providing a soft padding surface for padding the teeth against grinding. It will be understood that the guard 12 corresponds generally to a guard of any type that is fit to the teeth of the user by a boil and bite fitting method, in which the guard is heated to soften the guard material and then the user inserts the guard in the mouth and applies a biting pressure to conform portions of the guard to the teeth surfaces.

The material of the channel 16 may have a Vicat softening temperature of less than about 46° C., examples of which include ethylene vinyl acetate materials available from DuPont under the names ELVAX and AETVA. Such materials preferably have a Vicat softening point of between 36° C. and 46° C. and Shore A hardness of between 73 and 84. The material of the pad 18 may, for example, have a Vicat softening temperature of at least about 65° C., examples of which are ethylene methyl acrylate copolymers available under the name ELVALOY from DuPont. Such materials preferably have a Vicat softening point of between 65° C. and 75° C. and Shore A hardness of between 90 and 98. Pad 18 prevents the user from biting through the dental guard channel 16 during use.

Figure 5:
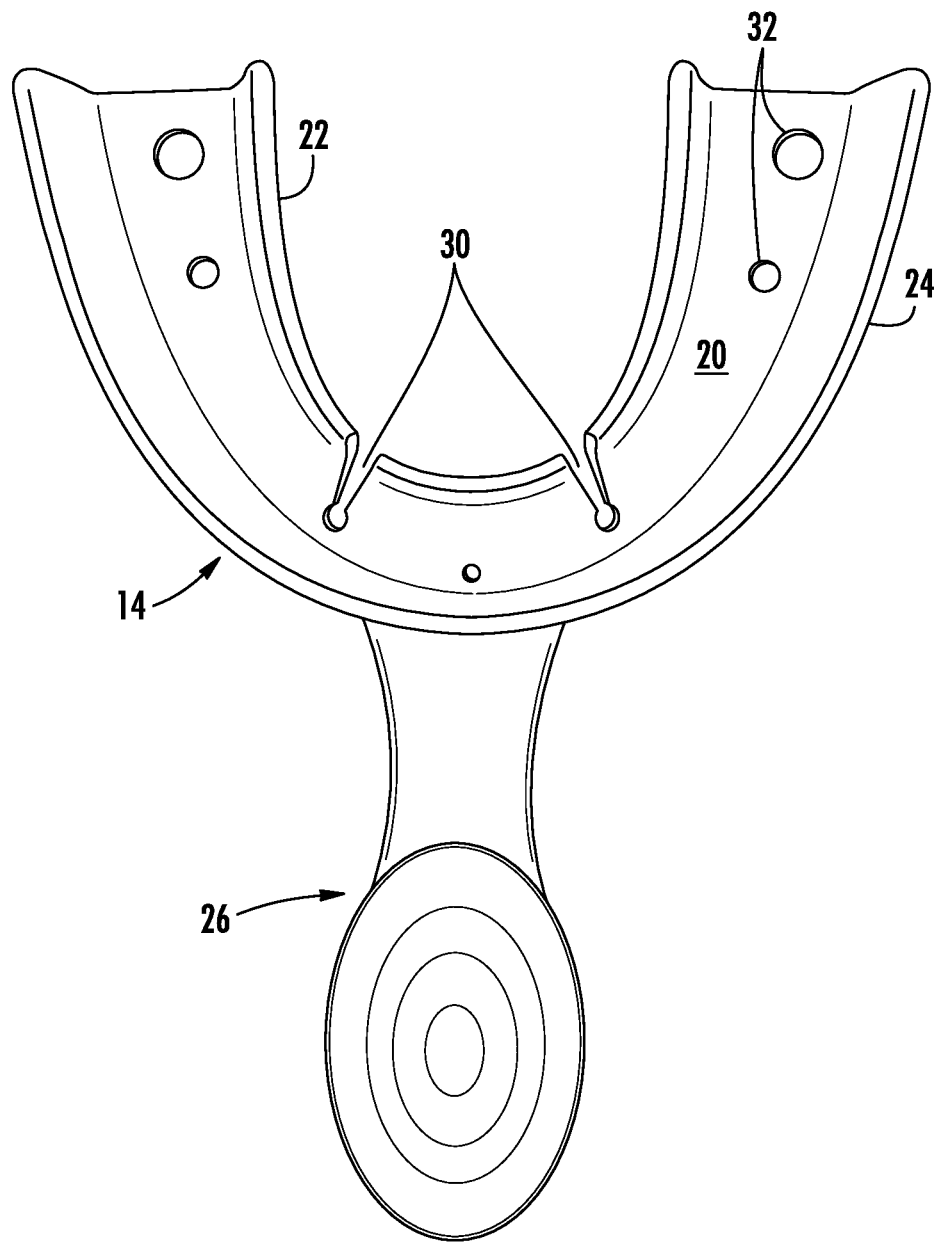
FIG. 5 is an upper plan view of a forming tray according to the disclosure.

With additional reference to FIG. 5, the forming tray 14 is made of a lightweight generally rigid material, such as injection molded plastic. The tray 14 is disposable and may be biodegradable. The forming tray 14 is configured to fittingly receive the dental guard 12 for heating and fitting thereof, with the guard 12 thereafter being removed from the tray 14 after the guard 12 is fitted to the user.

The tray 14 includes a generally planar base surface 20, a generally planar buccal sidewall 22 extending from one side of the base surface 20, and a generally planar lingual sidewall 24 extending from opposite side of the base surface 20. As the tray 14 is of a lightweight generally rigid material, the surface 20 may be slightly convex, so as to respond to a generally planar orientation and urge the buccal sidewall 22 and lingual sidewall 24 to a generally vertical orientation when a user applies a biting pressure to the guard 12 installed in the tray 14. A handle 26 extends from a front exterior sidewall of the tray 14. The handle 26 facilitates submersion of the tray into and removal from heated water and also positioning of the tray 14 with the guard 12 within the mouth of the user during fitting of the guard, and thereafter removal.

The tray 14 is configured to have a close interference fit with the guard 12. This is advantageous because the tray 14 remains with the guard 12 during heating of the guard 12 and thereafter fitting of the guard 12 to the teeth of the user. In this regard, the tray 14 is slightly smaller than the guard 12 and substantially thin and configured to flex to allow the tray 14 to expand slightly to receive the guard 12, and thereafter relax to grip and retain the guard 12. For example, the base surface 20 and the sidewall 22 include one or more slots 30 that enlarge in the direction from the base 20 toward the sidewall 22 to provide a hinge or flex point that permits the tray 14 to expand slightly to receive the guard 12, and thereafter relax to grip and retain the guard 12. The slots 30 are circular at their interior-most locations and taper outwardly in a pie-shape. The circular interior shape of the slots 30 is advantageous to provide a curved surface that tends to avoid tearing. Drainage apertures 32 are also provided on the base surface 20 to permit water to drain when the guard/tray combination is removed from the heating water.

The tray 14 is also dimensioned so that the sidewalls 22 and 24 of the tray 14 are substantially taller than the guard 12 to aid in forming of the guard 12 during fitting. That is, the tray 14 is tall enough so as to fully contain the guard 12 as it changes configuration during fitting such that portions of the guard 12 do not pass beyond the borders of the tray 14. However, the tray 14 is short enough to fit comfortably in the mouth. For example, the tray 14 preferably extends about ⅜ inches above the guard.

The tray 14 is "generally rigid" in that it tends to retain its shape so as to provide a guide to inhibit undesirable deformations of the guard 12, yet provides the described close interference fit with the guard 12 and enables the guard 12 to form to the teeth, the surrounding tissue and the supporting structure of the user. However, when exposed to a biting pressure, such as seen in FIG. 4B, the tray 14 will not substantially conform to the tooth surfaces applying the pressure. Tray 14 has a Vicat softening temperature and a Shore A hardness at least equal to or greater than the Vicat softening temperature and Shore A hardness of the pad 18 but greater than the material of channel 16.

Figure 3B:
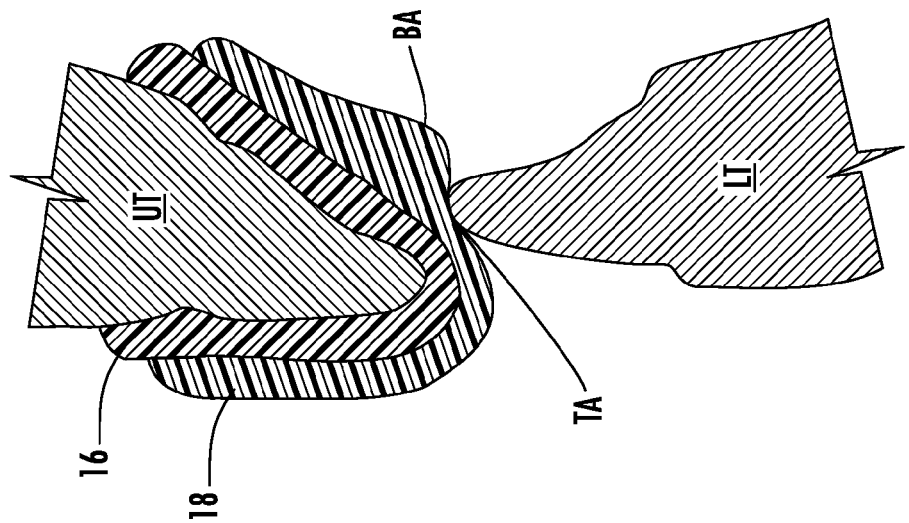
FIG. 3B is a cross-sectional view showing undesired deformation of the dental guard of FIG. 3A.
Figure 3A:
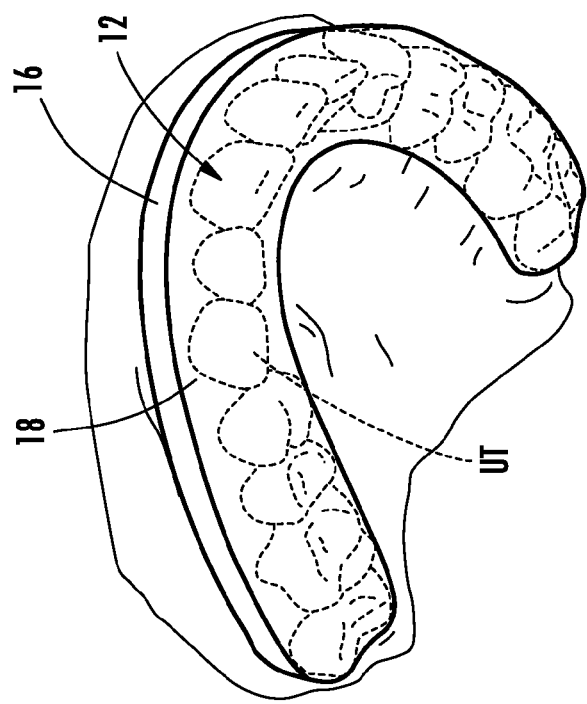
FIG. 3A is a perspective view showing a boil and bite type dental guard applied to the teeth of a user in a prior art method that does not utilize a forming tray according to the disclosure.

With reference to FIGS. 3A and 3B, there is shown a boil and bite type dental guard 12 applied to the upper teeth UT of a user in a prior art method that does not utilize the forming tray 14 according to the disclosure. FIG. 3B is a cross-sectional view showing undesired deformation of the dental guard 12 when the forming tray 14 according to the disclosure is not utilized. As will be observed, at the juncture of the upper teeth UT with lower teeth LT, a bulging area BA is seen and characterized by a bulge of material of the guard 12 and representing an undesirable deformation of the guard 12. In addition, as there is an excess of material of the guard 12 in the bulging area, there is a corresponding thin area TA adjacent the bulging area BA, typically at the pressure point represented by the intersection of the upper teeth UT and the lower teeth LT. This reduction in thickness at the meeting of the teeth is undesirable and can cause a weak point or tear in the guard 12, as well as generally poor performance of the guard 12 for its intended purpose. Furthermore, as seen in FIG. 3A, when the guard 12 includes the pad 18, the material of the pad 18 substantially deforms and migrates such that very little of the material of the pad 18 remains in its intended location.

FIGS. 4A-4C depict application of the guard 12 to the teeth of a user utilizing the forming tray 14 according to the disclosure. As will be observed in FIG. 4A and FIG. 4C, the material of the channel 16 does not undesirably migrate and remains in its intended location on the buccal and lingual walls. Pad 18 remains between the meeting upper UT and lower teeth LT. As will be appreciated, the surface 20 together with the buccal sidewall 22 and the lingual sidewall 24 tend to guide the material of the channel 16 to conform to the teeth, the surrounding tissue and the supporting structure and to not bulge outwardly. In this regard, it will be observed in FIG. 4B, that the forming tray 14 is "generally rigid" in that tray 14 will substantially conform the guard 12 to the tooth surfaces, the surrounding tissue and the supporting structure to provide a custom fit.

To effectively utilize the system 10 to fit the guard 12 to the user, the guard 12 and tray 14 are heated, as by immersing in boiling water for 10 seconds. The user then places the guard 12 and the tray 14 in the mouth aligned with the upper teeth. The user then applies a biting pressure for about 30 seconds to conform portions of the guard 12 to the adjacent tooth surfaces. The guard 12 and tray 14 are removed from the mouth and guard 12 is then removed from tray 14 which may thereafter be discarded. Alternatively, the user place could heat the guard 12 and then place the guard 12 in tray 14, which is then placed in the mouth of the user, aligned with the upper teeth UT. As before, the user applies a biting pressure for about 30 seconds, removes the tray and guard from the mouth, removed guard 12 from tray 14 and discard tray 14.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A dental guard system, comprising:
   a boil and bite dental guard made of a thermoplastic material that is softenable by immersion in heated water and capable of changing configuration when being fitted to a user by use of heating of the boil and bite dental guard followed by application of biting pressure by the user to conform portions of the boil and bite dental guard to tooth surfaces of the user; and
   a generally rigid forming tray made of injection molded plastic and configured to fittingly receive the boil and bite dental guard during heating and fitting of the boil and bite dental guard to teeth of the user, the generally rigid forming tray including a base and a sidewall including at least two spaced apart slots formed in the base and the sidewall that each enlarge in a direction from the base toward the sidewall to provide a flex point that permits the generally rigid forming tray to expand slightly to receive the boil and bite dental guard, and thereafter relax to grip and retain the boil and bite dental guard during heating and fitting of the boil and bite dental guard, the generally rigid forming tray remaining sufficiently rigid so that during fitting of the boil and bite dental guard the generally rigid forming tray does not substantially conform to the tooth surfaces of the user.

2. The dental guard system of claim 1 wherein at least a portion of the forming tray has a smaller diameter than a corresponding portion of the boil and bite dental guard it receives.

3. The dental guard system of claim 1 wherein the forming tray has a Vicat softening temperature and a Shore A hardness at least equal to the Vicat softening temperature and Shore A hardness of the boil and bite dental guard.

* * * * *